US00PP22837P2

(12) United States Plant Patent
Vlielander

(10) Patent No.: US PP22,837 P2
(45) Date of Patent: Jul. 3, 2012

(54) *KALANCHOE* PLANT NAMED 'FIKALMILAR'

(50) Latin Name: *Kalanchoe blossfeldiana*
Varietal Denomination: Fikalmilar

(75) Inventor: Ike J. Vlielander, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/931,626

(22) Filed: Feb. 3, 2011

(51) Int. Cl.
*A01H 5/00* (2006.01)

(52) U.S. Cl. ..... Plt./340

(58) Field of Classification Search ..... Plt./340
See application file for complete search history.

*Primary Examiner* — Annette Para
(74) *Attorney, Agent, or Firm* — C. A. Whealy

(57) ABSTRACT

A new and distinct cultivar of *Kalanchoe* plant named 'Fikalmilar', characterized by its compact, upright and uniformly mounded plant habit; moderately vigorous growth habit; freely branching plant habit; glossy green-colored leaves; uniform and freely flowering habit; large dark orange-colored flowers; and excellent postproduction longevity.

1 Drawing Sheet

Botanical designation: *Kalanchoe blossfeldiana.*
Cultivar denomination: 'FIKALMILAR'.

BACKGROUND OF THE INVENTION

The present invention relates to a new and distinct cultivar of *Kalanchoe* plant, botanically known as *Kalanchoe blossfeldiana* and hereinafter referred to by the name 'Fikalmilar'.

The new *Kalanchoe* plant is a naturally-occurring whole plant mutation of *Kalanchoe blossfeldiana* 'Milos', disclosed in U.S. Plant Pat. No. 16,482. The new *Kalanchoe* plant was discovered and selected by the Inventor as a single flowering plant from within a population of plants of the parent selection in a controlled environment in De Lier, The Netherlands in 2006.

Asexual reproduction of the new *Kalanchoe* plant by vegetative terminal cuttings in a controlled environment in De Lier, The Netherlands since 2006 has shown that the unique features of this new *Kalanchoe* plant are stable and reproduced true to type in successive generations.

SUMMARY OF THE INVENTION

Plants of the new *Kalanchoe* have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Fikalmilar'. These characteristics in combination distinguish 'Fikalmilar' as a new and distinct *Kalanchoe* plant:

1. Compact, upright and uniformly mounded plant habit.
2. Moderately vigorous growth habit.
3. Freely branching plant habit.
4. Glossy green-colored leaves.
5. Uniform and freely flowering habit.
6. Large dark orange-colored flowers.
7. Excellent postproduction longevity.

Plants of the new *Kalanchoe* can be compared to plants of 'Milos'. Plants of the new *Kalanchoe* differ from plants of 'Milos' in the following characteristics:

1. Plants of the new *Kalanchoe* have smaller leaves than plants of 'Milos'.
2. Plants of the new *Kalanchoe* and 'Milos' differ in flower color as plants of 'Milos' have yellow and orange bicolored flowers.

Plants of the new *Kalanchoe* can be compared to plants of *Kalanchoe blossfeldiana* 'Paso', disclosed in U.S. Plant Pat. No. 21,337. In side-by-side comparisons conducted in De Lier, The Netherlands, plants of the new *Kalanchoe* differed from plants of 'Paso' primarily in flower color as plants of 'Paso' have dark red-colored flowers.

BRIEF DESCRIPTION OF THE PHOTOGRAPH

The accompanying colored photograph illustrates the overall appearance of the new *Kalanchoe* plant showing the colors as true as it is reasonably possible to obtain in colored reproductions of this type. Colors in the photograph may differ slightly from the color values cited in the detailed botanical description which accurately describe the colors of the new *Kalanchoe* plant.

The photograph comprises a side perspective view of a typical flowering plant of 'Fikalmilar' grown in a container.

DETAILED BOTANICAL DESCRIPTION

The aforementioned photograph and following observations, measurements and values describe plants grown during the autumn in 10-cm containers in a glass-covered greenhouse in De Lier, The Netherlands and under conditions which closely approximate commercial *Kalanchoe* production. During the production of the plants, day temperatures ranged from 20° C. to 25° C., night temperatures ranged from 20° C. to 21° C. and light levels ranged from 10,000 lux to 50,000 lux. Plants received long day/short night conditions (more than 14 hours of light) for about four weeks then plants received photoinductive short day/long night conditions (minimum 14 hours darkness) until flowering. Plants were 13 weeks old when the photograph and the description were taken. In the detailed description, color references are made to The Royal Horticultural Society Colour Chart, 2007 Edition, except where general terms of ordinary dictionary significance are used.

Botanical classification: *Kalanchoe blossfeldiana* 'Fikalmilar'.

Parentage: Naturally-occurring whole plant mutation of *Kalanchoe blossfeldiana* 'Milos', disclosed in U.S. Plant Pat. No. 16,482.

Propagation:

*Type*.—By vegetative terminal cuttings.

*Time to initiate roots, summer*.—About twelve days at temperatures of 21° C.

*Time to initiate roots, winter*.—About 15 days at temperatures of 21° C.

*Time to produce a rooted young plant, summer*.—About three weeks at temperatures of 21° C.

*Time to produce a rooted young plant, winter*.—About four weeks at temperatures of 21° C.

*Root description*.—Fine, fibrous; greyish white in color.

*Rooting habit*.—Freely branching; dense.

Plant description:

*Plant and growth habit*.—Compact, upright and uniformly mounded plant habit; freely flowering habit with numerous racemes positioned above the foliar plane; inverted triangle with rounded crown; appropriate for 10 to 15-cm containers; moderately vigorous growth habit.

*Plant height at flowering*.—About 17 cm.

*Plant diameter at flowering*.—About 15 cm.

*Branching habit*.—Freely branching, usually about six to seven lateral branches develop per plant; pinching (removal of the terminal apex) is not required but will enhance lateral branch development.

Lateral branch description:

*Length*.—About 12 cm to 15 cm.

*Diameter*.—About 3 mm to 6 mm.

*Internode length*.—About 2 cm to 3 cm.

*Aspect*.—Erect.

*Strength*.—Strong.

*Texture*.—Smooth, glabrous.

*Color*.—Close to 138A.

Foliage description:

*Arrangement*.—Opposite, simple; generally symmetrical; mostly flat; glossy.

*Quantity per plant*.—About 8 to 13 mature leaves and about nine to 16 generative leaves.

*Length*.—About 10 cm.

*Width*.—About 7.5 cm.

*Shape*.—Ovate.

*Apex*.—Acute.

*Base*.—Obtuse.

*Margin*.—Slightly crenate.

*Texture, upper and lower surfaces*.—Smooth, glabrous; coriaceous; succulent.

*Venation pattern*.—Pinnate.

*Color*.—Developing and fully developed leaves, upper surface: Close to 138A; venation, close to 138A. Developing and fully developed foliage, lower surface: Close to 138B; venation, close to 138B.

*Petiole*.—Length: About 1.2 cm. Diameter: About 3 mm to 7 mm. Texture, upper and lower surfaces: Smooth, glabrous. Color, upper and lower surfaces: Close to 138A to 138B.

Flower description:

*Flower arrangement and habit*.—Flowers arranged singly in racemes that arise from leaf axils; uniform and freely flowering habit with usually about 25 open flowers and about 25 flower buds per lateral branch and more than 150 open flowers and flower buds per plant; flowering continuously for at least seven weeks.

*Fragrance*.—None detected.

*Natural flowering season*.—Plants of the new *Kalanchoe* initiate and develop flowers under short day/long night conditions or during November and December in The Netherlands; flower initiation and development can also be induced under artificial short day/long conditions (at least 14 hours of darkness).

*Time to flower*.—Under short day/long night photoinductive conditions, plants begin flowering in about eight to ten weeks; actual time to flower is primarily dependent upon temperature and light intensity.

*Post-production longevity*.—Excellent post-production longevity; plants maintain good foliage and flower substance for about 53 days under interior environmental conditions; individual flowers last about 18 days on the plant; flowers persistent.

*Flower diameter*.—About 1.7 cm.

*Flower length* (*height*).—About 1.4 cm.

*Flower bud*.—Shape: Initially oblong, becoming tubular ovoid with development. Length: About 1 cm. Diameter: About 4 mm. Color: Close to 138C and 33D.

*Petals*.—Arrangement: About four in a single whorl. Length: About 8.5 mm. Width: About 6 mm. Aspect: Flat to partially upright. Shape: Ovate. Apex: Acute. Margin: Entire. Texture, upper and lower surfaces: Smooth, glabrous. Color: When opening and fully opened, upper surface: Close to 33A; color becoming closer to 33B to 33C with development. When opening and fully opened, lower surface: Close to 29D and 32D.

*Sepals*.—Appearance: Four in a single whorl. Length: About 5 mm. Width: About 1.5 mm. Shape: Oblong, pointed. Apex: Acute. Base: Rounded. Margin: Entire. Aspect: Upright. Texture, upper and lower surfaces: Smooth; glabrous. Color, upper and lower surfaces: Close to 138D.

*Peduncles*.—Length: About 3 mm to 8 mm. Diameter: About 2 mm. Aspect: Erect. Strength: Strong. Texture: Smooth, glabrous. Color: Close to 138C.

*Reproductive organs*.—Androecium: Stamen number: About eight per flower. Anther shape: Elliptic, flat. Anther length: About 0.3 mm. Anther color: Close to 150D. Amount of pollen: Scarce. Pollen color: Close to 12A. Gynoecium: Pistil number: About four per flower. Pistil length: About 1 mm. Style length: About 1 mm. Style color: Close to 138D. Stigma shape: Flat. Stigma color: Close to 8D. Ovary color: Close to 138D.

*Seeds*.—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Fikalmilar' as illustrated and described.

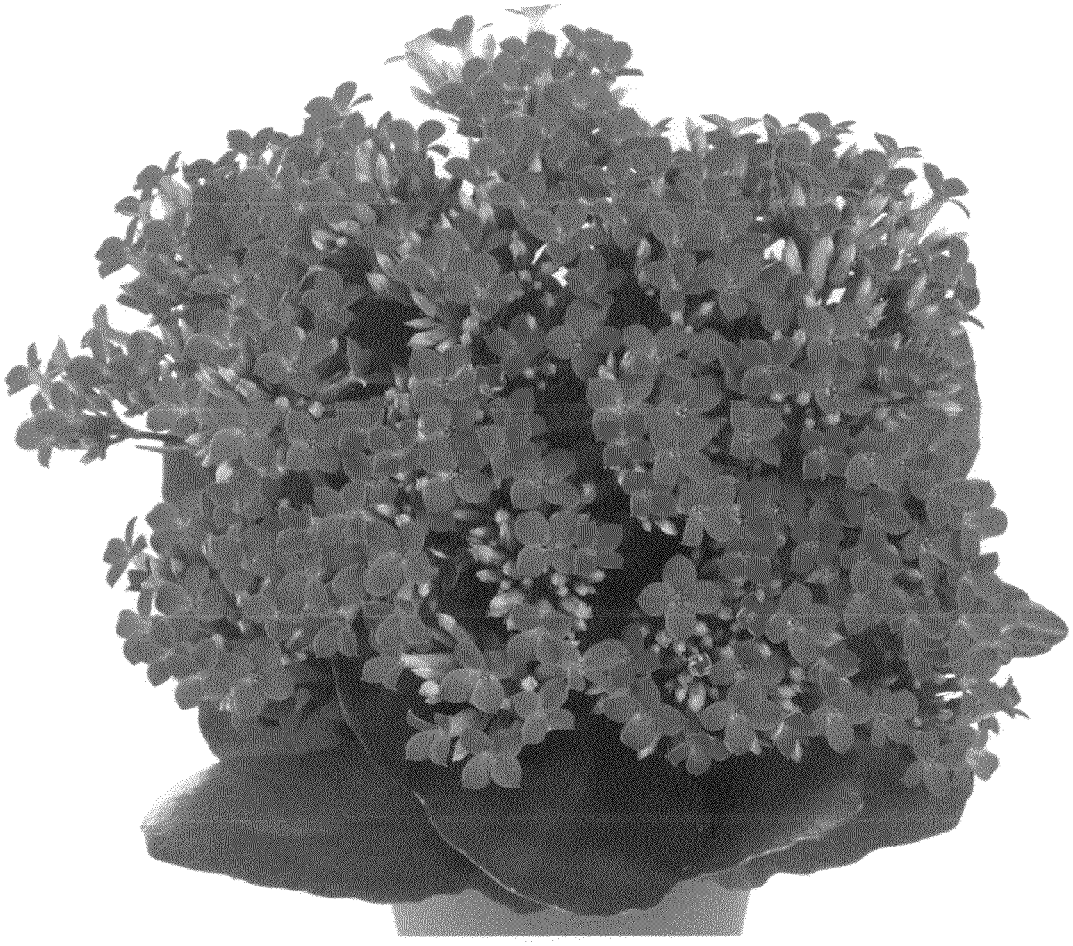

* * * * *